US012376613B2

(12) United States Patent
Maeda et al.

(10) Patent No.: US 12,376,613 B2
(45) Date of Patent: Aug. 5, 2025

(54) METHOD FOR PRODUCING WATER-SOLUBLE OR WATER-DISPERSIBLE MICROPARTICLES, USE OR METHOD FOR USE AS SUBSTITUTE HAVING EMULSIFYING FUNCTION, METHOD FOR PRODUCING EMULSION, METHOD FOR PRODUCING FOOD AND FOOD CONTAINING EMULSION

(71) Applicant: SAN-EI GEN F.F.I., INC., Toyonaka (JP)

(72) Inventors: Kazuhiro Maeda, Toyonaka (JP); Shingo Matsuyama, Toyonaka (JP); Satoshi Toyoizumi, Toyonaka (JP)

(73) Assignee: SAN-EI GEN F.F.I., INC., Toyonaka (JP)

( * ) Notice: Subject to any disclaimer, the term of this patent is extended or adjusted under 35 U.S.C. 154(b) by 1170 days.

(21) Appl. No.: 16/760,742

(22) PCT Filed: Oct. 3, 2018

(86) PCT No.: PCT/JP2018/037086
§ 371 (c)(1),
(2) Date: Apr. 30, 2020

(87) PCT Pub. No.: WO2019/087666
PCT Pub. Date: May 9, 2019

(65) Prior Publication Data
US 2020/0288759 A1 Sep. 17, 2020

(30) Foreign Application Priority Data

Nov. 2, 2017 (JP) ................................. 2017-212966
Apr. 10, 2018 (JP) ................................. 2018-075668

(51) Int. Cl.
A23L 29/10 (2016.01)
A23D 7/005 (2006.01)
A23L 15/00 (2016.01)
A23L 27/60 (2016.01)
A23L 29/30 (2016.01)
C09K 23/00 (2022.01)
C09K 23/30 (2022.01)
C09K 23/56 (2022.01)

(52) U.S. Cl.
CPC ............ *A23L 29/10* (2016.08); *A23D 7/0053* (2013.01); *A23L 15/35* (2016.08); *A23L 27/60* (2016.08); *A23L 29/30* (2016.08); *C09K 23/018* (2022.01); *C09K 23/30* (2022.01); *A23V 2002/00* (2013.01); *C09K 23/56* (2022.01)

(58) Field of Classification Search
CPC ........... A23L 29/10; A23L 27/60; A23L 15/35
See application file for complete search history.

(56) References Cited

U.S. PATENT DOCUMENTS

| 4,360,537 A * | 11/1982 | Tan .................... A23L 27/60 |
| | | 426/573 |
| 5,458,904 A | 10/1995 | Zolper |
| 6,743,945 B1 | 6/2004 | Takahashi et al. |
| 2007/0261293 A1 | 11/2007 | Tajima et al. |
| 2008/0009606 A1 | 1/2008 | Nakamura et al. |
| 2008/0299281 A1* | 12/2008 | Burger ................ A23L 29/10 |
| | | 426/654 |
| 2011/0236554 A1* | 9/2011 | Schmitt ............... A23L 33/18 |
| | | 435/68.1 |
| 2013/0274324 A1 | 10/2013 | Deng et al. |

FOREIGN PATENT DOCUMENTS

| GB | 1 440 181 A | 6/1976 |
| GB | 1 440 182 A | 6/1976 |
| JP | 10-168097 A | 6/1998 |
| JP | 10-237107 A | 9/1998 |
| JP | 2000-139344 A | 5/2000 |
| JP | 2006-239666 A | 9/2006 |
| JP | 2014-506126 A | 3/2014 |
| WO | 99/62935 A1 | 12/1999 |
| WO | 2004/078334 A1 | 9/2004 |
| WO | 2006/006521 A1 | 1/2006 |
| WO | 2017/170505 A1 | 10/2017 |

OTHER PUBLICATIONS

Sanchez et al. "Rheology of whey protein isolate-xanthan mixed solutions and gels. Effect of pH and xanthan concentration", Nahrung, vol. 41, No. 6, 1997, pp. 336-343.

Koutina et al., "The effect of alginates on in vitro gastric digestion of particulated whey protein", International Journal of Dairy Technology, vol. 71, No. 2, May 2018, pp. 469-477.

Nakagawa et al., "Protein-Based Microencapsulation with Freeze Pretreatment: Spray-Dried Oil in Water Emulsion Stabilized by the Soy Protein Isolate-Gum Acacia Complex", Drying Technology, vol. 33, 2015, pp. 1541-1549 (10 pages).

Zou et al., "Encapsulation of protein nanoparticles within alginate microparticles: Impact of pH and ionic strength on functional performance", Journal of Food Engineering, vol. 178, 2016, pp. 81-89.

Communication issued Jul. 28, 2021 by the European Patent Office in application No. 18874408.0.

Office Action dated May 19, 2021 issued by the Chinese Patent Office in Chinese Application No. 201880064593.4.

(Continued)

Primary Examiner — Jeffrey P Mornhinweg
(74) Attorney, Agent, or Firm — Sughrue Mion, PLLC

(57) ABSTRACT

A method for producing water-soluble or water-dispersible microparticles, which includes preparing a solution or dispersion that contains a protein and an anionic polysaccharide and that has a pH higher than the isoelectric point of the protein, and mixing the solution or dispersion to set the pH of the solution or dispersion to a value closer to the isoelectric point.

18 Claims, 3 Drawing Sheets

(56) References Cited

OTHER PUBLICATIONS

Zhao et al., "Effect of Polysaccharides on Emulsifying Properties of Soy Protein in Aqueous Media", Science and Technology of Food Industry, Mar. 31, 2002, vol. 1.23, No. 6, pp. 31-34 (4 pages).
International Search Report of PCT/JP2018/037086 dated Jan. 8, 2019 [PCT/ISA/210].

* cited by examiner

A photograph in which about 10 g of a sample is extruded from a star-shaped cap for mayonnaise and shows the state after 5 minutes The shear rate dependency of viscosity of the mayonnaise-like seasonings The strain-dependence for a storage modulus of a mayonnaise-like seasoning The observation results using an optical microscope (magnification: x150)

METHOD FOR PRODUCING WATER-SOLUBLE OR WATER-DISPERSIBLE MICROPARTICLES, USE OR METHOD FOR USE AS SUBSTITUTE HAVING EMULSIFYING FUNCTION, METHOD FOR PRODUCING EMULSION, METHOD FOR PRODUCING FOOD AND FOOD CONTAINING EMULSION

CROSS REFERENCE TO RELATED APPLICATIONS

This application is a National Stage of International Application No. PCT/JP2018/037086, filed Oct. 3, 2018, claiming priority to Japanese Patent Application No. 2017-212966, filed Nov. 2, 2017 and Japanese Patent Application No. 2018-075668, filed Apr. 10, 2018.

TECHNICAL FIELD

The present invention relates to a method for producing water-soluble or water-dispersible microparticles, a method for use or a use as a substitute having an emulsifying function, a method for producing an emulsion, a method for producing a food, and a food containing an emulsion.

BACKGROUND ART

Conventionally, various emulsifiers and/or emulsifying methods have been investigated, and longstanding known examples include emulsifying methods using microparticles. In addition, a three-phase emulsification method has been proposed in which an emulsion is created by substitution of a surfactant with nanoparticles of an amphiphilic compound that exist as an independent phase in an oil/amphiphilic compound/water system and are adhered to the surface of an oil base by van der Waals force (reference is made to Patent Document 1).

Irrespective of the type of product to be emulsified or the field of use, the production of W/O type or O/W type emulsions is demanded the development of simple and inexpensive new methods that exhibit excellent stability over time.

CITATION LIST

Patent Literature

[Patent Literature 1] Japanese Patent Application Laid-Open No. 2006-239666

SUMMARY OF INVENTION

Technical Problem

The present disclosure has the object of providing a method for producing water-soluble or water-dispersible microparticles that exhibit excellent stability over time, a method for use or a use thereof as a substitute having an emulsifying function, a method for producing an emulsion, a method for producing a food, and a food containing an emulsion.

Solution to Problem

The present disclosure includes the following inventions.

(1) A method for producing water-soluble or water-dispersible microparticles comprising;

preparing a solution or dispersion that contains a protein and an anionic polysaccharide and that has a pH higher than the isoelectric point of the protein, and mixing the solution or dispersion to set the pH of the solution or dispersion to a value closer to the isoelectric point.

(2) The method for producing water-soluble or water-dispersible microparticles as the above, wherein the preparation of the solution or dispersion includes the steps of preparing a solution of protein, preparing a solution or dispersion of anionic polysaccharides, and obtaining a mixed solution containing the protein and an anionic polysaccharide while maintaining a pH that is higher than the isoelectric point of the protein.

(3) The method for producing water-soluble or water-dispersible microparticles as the above, wherein the protein solution is prepared at a pH higher than the isoelectric point of the protein.

(4) The method for producing water-soluble or water-dispersible microparticles as the above, wherein the protein solution is prepared at a pH that is greater than or equal to a value that is one higher than the isoelectric point of the protein.

(5) The method for producing water-soluble or water-dispersible microparticles as c the above, wherein the protein solution is prepared at a concentration of 0.01 w/w % to 5 w/w %.

(6) The method for producing water-soluble or water-dispersible microparticles as the above, wherein the solution or dispersion of the anionic polysaccharide is prepared at a concentration of 0.005 w/w % to 5 w/w %.

(7) The method for producing water-soluble or water-dispersible microparticles as the above, wherein the protein and the anionic polysaccharide are mixed at a mass of 2:98 to 95:5.

(8) The method for producing water-soluble or water-dispersible microparticles as the above, wherein in the step of mixing the solution or dispersion to set the pH of the solution or dispersion to a value closer to the isoelectric point, the solution or dispersion is stirred after setting the pH of the solution or dispersion to a value closer to the isoelectric point.

(9) The method for producing water-soluble or water-dispersible microparticles as the above, wherein in the step of mixing the solution or dispersion and setting the pH of the solution or dispersion to a value closer to the isoelectric point, a homomixer is used for the mixing.

(10) The method for producing water-soluble or water-dispersible microparticles as the above, wherein the protein is at least one selected from the group consisting of casein sodium, alkali-treated gelatin, acid-treated gelatin, whey protein, soy protein, acid-soluble soy protein and pea protein.

(11) The method for producing water-soluble or water-dispersible microparticles as the above, wherein the anionic polysaccharide is at least one selected from the group consisting of xanthan gum, welan gum, carrageenan, deacylated gellan gum, native gellan gum, rhamsan gum, pectin, alginic acid, alginate, tragacanth gum, gati gum, gum arabic, arabinogalactan, karaya gum, succino glycans, cellulose derivatives, starch derivatives and soybean polysaccharides.

(12) Use of an emulsifying functional substitute for egg yolk of the water-soluble or water-dispersible microparticles as the above.

(13) A method for using an egg yolk substitute as an emulsifier of the water-soluble or water-dispersible microparticles obtained by the method of the above.

(14) A method for producing an emulsion comprising mixing a combination of an oil with the water-soluble or water-dispersible microparticles obtained by the method of the above.

(15) The method for producing an emulsion as the above, wherein
the emulsion is a substitute for the emulsifying function of egg yolk.

(16) A method for producing a food comprising adding the emulsion obtained by the method for producing an emulsion of the above.

(17) A food comprising the emulsion obtained by the method for producing an emulsion of the above.

Advantageous Effects of Invention

The present disclosure enables provision of a method for producing water-soluble or water-dispersible microparticles that are attached to the surface of oil droplets and function as an emulsifier, a method for producing an emulsion that exhibits superior temporal stability in which the oil phase and the water phase do not separate for a long time as a result of the water-soluble or water-dispersible microparticles, a method for use or a use as a substitute having an emulsifying function, a method for producing a food, and a food containing an emulsion.

DESCRIPTION OF EMBODIMENTS

Figure 1:
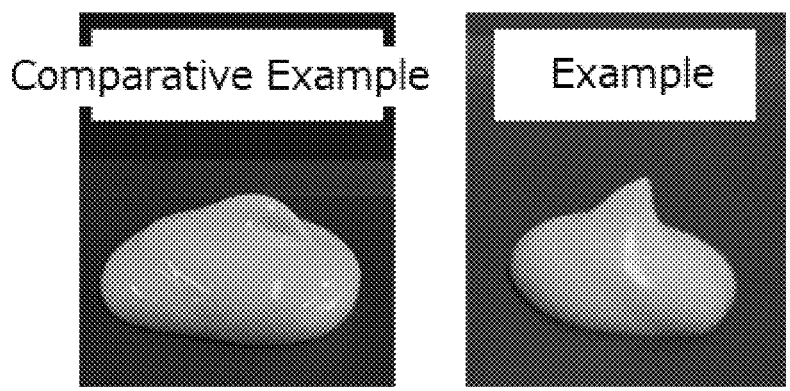
FIG. 1 is a photograph in which about 10 g of a sample is extruded from a star-shaped cap for mayonnaise in Example D, and shows the state after 5 minutes (left: Comparative Example 8, right: Example 8).

[Method for Producing Water-Soluble or Water-Dispersible Microparticles]

The method for producing water-soluble or water-dispersible microparticles of the present disclosure mainly comprises preparing a solution or dispersion containing a protein and an anionic polysaccharide and having a pH higher than the isoelectric point of the protein, and bringing the pH of this solution or dispersion close to the isoelectric point as described above. At this time, the pH may be brought close to the isoelectric point while stirring the solution or dispersion, or the stirring may be carried out after the pH has been brought close to the isoelectric point.

In particular, this production method has the unexpected result of producing microparticles in a uniform and fine state without producing protein and/or polysaccharide aggregates due to the fact that the solution or dispersion is mixed and the pH of the solution or dispersion is configured close to the isoelectric point of the protein. Furthermore, the resulting microparticles exhibit long-term stability.

In addition, when the microparticles obtained in this way are used for emulsification, they can function as an emulsifier which adheres to the oil drop surface and maintains the stability of the emulsion. Furthermore, since microparticles can also be produced by components conventionally used as a food, such as proteins and polysaccharides, or the like, they can be used in various applications in which an emulsifying agent has conventionally been used, and in particular, in relation to foods such as liquid foods, mayonnaise, dressings, ice cream, or the like, emulsified flavors and emulsified dyes, or the like. Moreover, in addition to foods, use is possible in applications in various fields including industrial products such as waxes and paints, or the like as well as cosmetics and pharmaceuticals.

For example, when the microparticles obtained in this manner are used in an emulsification, they exhibit excellent emulsion stability in relation to salt resistance, acid resistance and heat resistance, or the like. Therefore, the microparticles can be used for the preparation of mayonnaise with reduced oil separation, and use is also possible in relation to pack filling or hot pack filling as a dressing, pasta sauce or the like which exhibits high oil suspension stability and superior flavoring. Furthermore, use is also possible as a substitute for an egg yolk emulsifying function.

The isoelectric point in the present application means a pH at which the charge average of the solution after ionization has a value of zero in an amphoteric electrolyte solution such as a protein or the like. For example, it is known that whey protein has an isoelectric point of about 4.5 to 5.0, and casein Na has an isoelectric point of about 4.6.
(Preparation of Solution or Dispersion)

First, a solution or dispersion containing a protein and an anionic polysaccharide and having a pH higher than the isoelectric point of the protein is prepared. Hereinafter, the pH at this time may be described as "initial pH."

Proteins that can be used in the method for producing water-soluble or water-dispersible microparticles include various proteins in addition to the proteins that can be used in the field of foods. For example, any simple proteins, complex proteins, induced proteins, or the like may be used. Proteins for use include albumin, globulin, glutelin, prolamin, hard protein (collagen, elastin, keratin etc.), glycoprotein (ovom colloid, mucin), phosphoprotein (casein), chromoprotein (hemoglobin, myoglobin), lipoprotein (lipobiterin, lipoprotein), metal proteins (ferritin, hemocyanin), gelatin, or the like. These may be used singly or in combinations of two or more. Of the above proteins, at least one type selected from the group consisting of casein, casein sodium, gelatin, alkali-treated gelatin, acid-treated gelatin, whey protein, soy protein, acid-soluble soy protein and pea protein is preferred.

The anionic polysaccharide is a polysaccharide having a negative charge in its molecular structure, and includes, for example, at least one selected from the following groups:

polysaccharides produced by microorganisms including xanthan gum, deacylated gellan gum, native gellan gum, rhamsan gum, succinoglycan, welan gum, or the like, and plant-derived polysaccharides including pectin (derived from fruit peel), tragacanth gum, gum arabic, arabinogalactan, gati gum, karaya gum (derived from sap), alginic acid, alginate, carrageenan (derived from seaweed), soybean polysaccharide (derived from seed), cellulose derivatives and starch derivatives (semi-synthetic products of plant origin) or the like.

In this context, the term "derivative" as used herein means a compound in which a part of the compound is substituted by another atom or atomic group, and in the present application, denotes all compounds in which a part of the atom or atomic group in a polysaccharide is substituted by an atomic group exhibiting anionic characteristics. An atomic group which exhibits an anionic property includes for example a carboxyl group.

In a solution or dispersion containing a protein and an anionic polysaccharide, the protein may have a concentration not higher than the concentration at which it becomes a saturated solution, and includes for example, a concentration of 0.01 w/w % to 5 w/w %.

The concentration of the solution or dispersion containing the anionic polysaccharide for example may be 0.005 w/w % to 5 w/w %.

The ratio of the protein to the anionic polysaccharide is a mass ratio from 2:98 to 95:5, preferably from 10:90 to 90:10, and more preferably from 20:80 to 80:20.

The preparation of a solution or dispersion containing a protein and an anionic polysaccharide and having a pH higher than the isoelectric point of the protein may be configured by (a) preparing a mixed solution in the state where the protein and polysaccharide coexist, and (b) preparing a protein solution and a polysaccharide solution or dispersion separately, and mixing these solutions to prepare a mixed solution.

In a solution or dispersion containing a protein and an anionic polysaccharide, the protein is completely or almost completely dissolved because the solution or dispersion has a higher pH than the isoelectric point of the protein, that is to say, the initial pH. In addition, the anionic polysaccharide may be completely or almost completely dissolved as a solution or dispersion, or it may be floated or suspended without being partially or completely dissolved.

The solvent for the solution or dispersion containing the protein and the anionic polysaccharide can be appropriately selected from water, an organic solvent and a combination thereof, with water (for example, ion-exchanged water, pure water, distilled water, ultrapure water, tap water, or the like) being preferred. As described above, the pH of the solvent may be adjusted by inclusion of a pH adjusting agent such as citric acid, gluconic acid, succinic acid, potassium carbonate, sodium hydrogen carbonate, carbon dioxide, lactic acid, phosphoric acid, adipic acid, trisodium citrate, sodium malate, or the like.

In light of described above, when both the protein and anionic polysaccharide are included, the protein may be dissolved in the solvent, and the anionic polysaccharide can take the form of a dispersion in the solvent.

When a solution or dispersion containing a protein and an anionic polysaccharide is prepared by preparing separate solutions or dispersions containing the protein and the anionic polysaccharide and then mixing those solutions or dispersions to prepare a mixed solution, the protein solution preferably maintains a higher pH than the isoelectric point of the pH of the protein. A pH that is higher than the isoelectric point of the protein is preferably at least a pH that is a value of one greater, and more preferably at least 1.4 greater or at least 1.5 greater. On the other hand, the protein solution preferably has a pH that is lower than 9.0, and more preferably a pH that is lower than 7.0.

It is noted that even when preparing both the protein and the anionic polysaccharide as a mixed solution, it is preferred that the pH of the mixed solution is maintained at a pH higher than the isoelectric point of the protein as described above.

Furthermore, at preparing a solution or dispersion containing an anionic polysaccharide, when the anionic polysaccharide dissolves in a solvent, it is preferred in a form of a solution, and when it does not dissolve in a solvent, it is preferred to apply a suitable force to form a dispersion. The force applied in this context includes, for example, known methods for preparing a dispersion of polysaccharides such as propeller stirring while heating, stirring with a homomixer, homogenization using a homogenizer, or the like.

The solvent for dissolving the protein and the solvent containing the anionic polysaccharide may be the same or different, but it is preferred that both are the same, and it is more preferred that it is water.

When mixing these two types of solutions or dispersions, it is preferred to mix while maintaining the pH higher than the isoelectric point of the protein, that is to say, while maintaining the initial pH, to thereby configure a mixed solution. The mixing may mix both uniformly. The mixing may be manual, or a mixer or mixing device known in this technical field may be used. The mixing may be performed by any of stirring (shearing), shaking, injection, sonication or the like. For example, a propeller stirrer, a homomixer, a homogenizer or the like can be used. The mixing in this case may apply a load which is greater than or equal to a load which both are uniformly mixed. For example, this may include homogenizer treatment at a pressure of about 5 MPa to 50 MPa and mixing at about 5000 rpm to 35000 rpm for several tens of seconds to several hours. The temperature in this case may range from a temperature at which the solution does not freeze to a temperature at which the protein does not denature, for example, a range from room temperature to 80° C.

(Adjustment of pH of Solution or Dispersion)

Next, the pH of a solution of the protein solution described above and a solution or dispersion of an anionic polysaccharide, or a mixed solution containing a protein and an anionic polysaccharide is configured to a value that is closer to the isoelectric point of the protein. In this case, a pH adjusting agent may be added. When configuring the pH to a value closer to an isoelectric point of the protein, it is preferred to perform mixing so that the pH is uniform throughout the whole liquid.

For example, the pH of the solution or dispersion of the anionic polysaccharide may not necessarily correspond to the pH of the solution of the protein. However, irrespective of the pH of the solution or dispersion of the anionic polysaccharide, a pH adjusting agent is added so that the pH of the mixed solution containing both components has a pH at which the protein does not precipitate. And then, the final pH of the mixed solution is adjusted more closely to the isoelectric point of the protein than the initial pH.

Furthermore, since the pH of a mixed solution containing the protein and the anionic polysaccharide is set higher than the isoelectric point of the protein, that is to say, since it is set to the initial pH, the pH of the mixed solution is lowered enough to avoid precipitation of the protein and it is configured more closely to the isoelectric point of the protein than the initial pH.

In this context, setting the pH of the solution more closely to the isoelectric point means that the difference between the pH of the resulting mixed solution and the isoelectric point is smaller than the difference between the initial pH and the isoelectric point of the protein that is used. For example, the initial pH may be higher than the isoelectric point, and the pH of the resulting mixed solution may be higher than or equal to the isoelectric point, or the initial pH may be higher than the isoelectric point, and the pH of the resulting mixed solution may be lower than the isoelectric point.

When the pH of the solution is configured closer to the isoelectric point of the protein relative to the initial pH, a shear force is applied to the solution by mixing. That is to say, the pH may be configured closer to the isoelectric point of the protein while mixing or stirring that applies a larger shear force to the mixed solution, or after the pH is configured closer to the isoelectric point of the protein, mixing or stirring may be performed to apply a larger shear force. The shear force in this context is preferably a larger load than that a load enabling uniform mixing in a configuration in which separate protein solutions and the anionic polysaccharide solutions or dispersions are prepared, and then both are mixing, as described above, and for example, it is preferably by high speed stirring and high shear force. For this purpose, examples include stirring with a screw with a blade, circulation agitation with a high shear mixer such as a homomixer, and homogenization using an apparatus such as a homogenizer or a high-pressure homogenizer.

For example, mixing may be performed at 5000 rpm to 35000 rpm in a temperature range of room temperature to less than or equal to the denaturation temperature of the protein, for example, in a temperature range from room temperature to 80° C. for several tens of seconds to several tens of hours.

So-called built-up type microparticles can be formed by mixing as a mixed solution containing a protein and an anionic polysaccharide while adjusting the shear force and pH. That is to say, by mixing these substances, the protein and the anionic polysaccharide are dispersed in the solvent in the form of fine particles due to aggregation and self-association.

In this context, the microparticles are configured as a complex resulting from electrostatic interaction of the protein with the anionic polysaccharide. For example, the size may be 10 nm to 1000 μm in diameter, preferably 50 nm to 500 μm in diameter, and more preferably 100 nm to 100 μm in diameter. The size of the resulting microparticles can be adjusted by the shear force and the time of its application.

Although the microparticles obtained in this manner exhibit various properties such as water solubility, water insolubility, water dispersibility, or the like, they have an emulsifying action that forms W/O type, O/W type and W/O/W type emulsions, and therefore they can be used as an emulsifier.

Furthermore, the microparticles obtained in this manner can be used as a substitute for emulsifiers currently used in the food industry, or the like, and specifically, can be used as a substitute for synthetic surfactants such as sucrose fatty acid esters and glycerin fatty acid esters, or the like, natural polysaccharides such as gum arabic, or the like, and natural protein materials such as egg yolk and soybean lecithin, or the like.

(Method for Producing Emulsion)

An emulsion can be produced by blending and mixing an oil with the water-soluble or water-dispersible microparticles obtained using the method above.

When an oil is blended with the water-soluble or water-dispersible microparticles, only the microparticles may be extracted and added to a solution containing oil and water, or a solution containing oil and water may be added to the microparticles. A mixed solution containing the microparticles may be added without modification to the oil, or an oil may be added to a mixed solution containing the microparticles. A method for extracting only microparticles for example includes formation of a powder of a mixed solution containing the microparticles by spray drying, freeze drying, ethanol precipitation, or the like. The mass ratio of the microparticles to the oil is 0.1:99.9 to 99:1, is preferably 0.5:99.5 to 99:1, and is more preferably 1:99 to 99: 1.

The term "emulsification" in the present invention means a general emulsification, that is to say, a configuration in which one of two liquids that do not dissolve in each other is evenly dispersed in the other (Source: Daijirin) and includes a configuration in which the dispersed is uniformly dispersed in the dispersion medium. Therefore, the emulsion is considered to be in a stable state when only a layer of the dispersion medium (also termed top transparence and bottom transparence) is formed, and the emulsion state in the present invention is determined to be stable as long as there is no production of a layer of only the other component in which the emulsified particles are collapsed and do not dissolve in the dispersion medium. More specifically, in the case of O/W type emulsion, it is determined that the emulsion is kept stable because that the emulsified particles are not disintegrated only by the formation of an aqueous layer (dispersion medium). On the other hand, it is determined that the emulsion cannot be kept stable because that the emulsified particles are disintegrated by the formation of an oil layer (dispersoid) due to coalescence.

Furthermore, the preparation of the microparticles and the preparation of the emulsion may be carried out at the same time by creating a mixture containing a protein solution, an anionic polysaccharide solution or dispersion, and oil or a mixture of water and oil.

From another point of view, the mass ratio of oil to protein contained in the microparticles may be 0.05: 99.95 to 99:1, preferably 0.25: 99.75 to 99:1, and more preferably 0.5: 99.5 to 99:1.

The mass ratio of the anionic polysaccharide contained in the microparticles to oil is for example, 0.05: 99.95 to 99:1, preferably 0.25: 99.75 to 99:1, and more preferably 0.5:99.5 to 99:1.

From still another viewpoint, the mass ratio of the mixture containing microparticles to oil may be 1:99 to 99:1, preferably 10:90 to 99:1, and more preferably 20:80 to 99:1.

By mixing both in such a mass ratio, it is possible to produce a uniform emulsion that exhibits long-term stability.

There is no particular limitation in relation to the oil, and the oil may include oils that are used in the above-mentioned applications. Examples include mineral oils (for example, naphtha, gasoline, light oil, kerosene, heavy oil, mineral oil, paraffin, silicone oil, shale oil, or the like), vegetable oils (for example, canola oil, coconut oil, corn oil, cottonseed oil, olive oil, palm oil, peanut oil, sunflower oil, soybean oil, safflower oil, rice oil, sesame oil, or the like), animal oils (for example, lard, beef tallow, butter, liver oil, beeswax, or the like) and combinations thereof. The oil may contain oil soluble ingredients (for example, a carotenoid, or the like). Furthermore, the oil may be an oil used for any of a food, cosmetics, a fuel or an industrial use. The oil may be in various forms such as fluid, semi-fluid, solid, finely-divided solid, or the like.

The mixing in this context is preferably performed to the extent necessary to emulsify the oil. For example, it is preferred to use high speed stirring or a high shear force. Consequently, it includes for example, stirring using a screw with a blade, circulation stirring with a high shear mixer such as a homomixer, homogenization using a homogenizer, or the like. Homogenization using a homogenizer can be carried out using equipment such as a high-speed stirrer, a homomixer, a high-pressure homogenizer, or the like in order to finely divide and homogenize the resulting particles.

For example, it is preferred to homogenize with a homogenizer at a pressure of about 5 MPa to 15 MPa or to perform stirring with a homomixer at about 5000 rpm to 15000 rpm.

When making water-soluble or water-dispersible microparticles and emulsions, the stability can be enhanced by homogenizing and/or heat treating (for example, at 85° C. for 30 minutes) with a high-pressure homogenizer (for example, 20 MPa to 50 MPa).

A microparticle emulsion exhibits heat resistance and acid resistance. For example, after adjusting the microparticle emulsion to a pH of 4.0~7.0, an aggregate is not produced even if retort treatment (10 minutes at 121° C.) is performed, and a stable emulsified state can be maintained.

In addition, the microparticle emulsion exhibits salt resistance. For example, a microparticle emulsion prepared by using a combination of acidic polysaccharides such as xanthan gum and carrageenan can maintain a stable emulsified state even when 3 wt% table salt is added.

[Food Containing Emulsion, and Method for Producing Same]

A food containing an emulsion or to which the emulsion is added according to the invention of the present application can not only be obtained by addition of an emulsion made by the above-mentioned production method but also by simultaneously mixing various components used in foods with water-soluble or water-dispersible microparticles, and an oil, or the like at producing the above emulsion.

The resulting microparticles can maintain emulsion stability when used in an emulsification.

The present invention may be used in relation to various foods in which an emulsifier is conventionally used, foods in a liquid state or seasonings containing oils, typically foods such as liquid foods, mayonnaise, dressings, pasta sauce, ramen soup, ice cream, or the like. For example, uses include breads, cakes (foam stability improvement); flour pastes; desserts such as whipped cream and butter cream; margarine, shortening, cooking oil, or the like; coffee cream; tofu; jams; kneaded foods such as sausages, chikuwa, kamaboko, frozen surimi, or the like; sweets such as chewing gum, chocolate, cookies, or the like; and various beverages, or the like.

EXAMPLES

Hereinafter, the present invention will be described in further detail using an example of a method for producing water-soluble or water-dispersible microparticles and a method for producing an emulsion. However, these examples do not limit the present invention. In addition, "%" in the Examples means "mass (w/w)%."

Example A (Preparation of Mixed Solution of Xanthan Gum and Protein)

Xanthan gum (Tradename: San Ace C, Source: San-Ei Gen F. F. I. Inc.) was added to ion-exchanged water heated to 80° C. to a concentration of 0.167%, obtained solution was stirred for 10 minutes at 80° C. to dissolve, and then cooled to room temperature (the pH of xanthan gum aqueous solution is about 6.5).

Alternatively, the protein shown in the following table was dissolved in ion exchanged water at room temperature to a concentration of 2.0% and obtained solution was adjusted to the pH to 6.5 to 7.0 with an aqueous solution of NaOH.

The resulting xanthan gum aqueous solution and protein solution were mixed at a mass ratio of 9:1, and pre-stirred at 400 rpm for 10 minutes until uniform using a four-blade screw. After adding and mixing a preservative of 0.2% of phenoxyethanol, principal stirring was performed by homomixer treatment at 9000 rpm for 3 minutes to obtain water-soluble or water-dispersible microparticles. At this time, an aqueous citric acid solution was added during homomixer treatment to adjust a pH of the mixed solution to any of 3.0, 3.5, 4.0, 4.5, 5.0, 5.5, 6.0, 6.5

(Preparation of Emulsion)

ODO (oil phase) was added to the resulting xanthan gum and proteins mixed solution (water phase) at a mass ratio of 4:1, and homomixer treatment was applied at 9000 rpm for 3 minutes to obtain O/W type emulsion.

The median diameter (units: um) of the emulsion the day after, and two weeks after, the preparation of the resulting emulsion was measured with a laser diffraction type particle size distribution analyzer SALD-2100 (manufactured by Shimadzu Corp.).

Furthermore, the emulsion was allowed to stand at room temperature (25° C.) for 1 month for visual confirmation of the state of emulsification.

The results are shown in the table below.

The "rate of change" in the table is the average particle size 2 weeks after preparation divided by the average particle size the day after preparation. A value of less than 1.5 is determined as "emulsion stability is maintained." In the table, "–" indicates that the particle size could not be measured because the emulsion composition had undergone oil phase separation 2 weeks after preparation.

Evaluation of the separation state was determined based on the following criteria.

In Tables 1 to 6, "separation" means a state in which separation of the oil phase was observed due to coalescence of the emulsified particles, and re-dispersing did not occur even after stirring. The term "bottom transparence" means that oil droplets float as a result of difference in the specific gravity between the oil phase and the water phase, and therefore the emulsion is concentrated, and will re-disperse with weak stirring. If the emulsion layer is stable, the emulsion state is considered to be stable even if the bottom transparence occurs. "No separation" is a state in which there is neither separation of the oil phase nor the bottom transparence due to creaming, and the oil phase is uniformly dispersed in the water phase.

In the table,
⊚: No separation,
○: Bottom transparence has occurred,
x: Separated.

TABLE 1

Casein Sodium (Tradename: Casein Sodium AR, Source: San-Ei Gen F. F. I. Inc.) (Isoelectric point: 4.6)

|  | Comp. Ex 1-1 | Examples | | | | Comp. Exs. | | |
|---|---|---|---|---|---|---|---|---|
|  |  | 1-1 | 1-2 | 1-3 | 1-4 | 1-2 | 1-3 | 1-4 |
| pH | 6.5 | 6.0 | 5.5 | 5.0 | 4.5 | 4.0 | 3.5 | 3.0 |
| Particle size the day after | 9.6 | 21.9 | 29.6 | 27.1 | 37.7 | Separated | Separated | Separated |
| Particle size 2 weeks after | 14.9 | 25.7 | 30.6 | 26.1 | 30.1 | Separated | Separated | Separated |
| Rate of Change | 1.56 | 1.17 | 1.03 | 0.96 | 0.80 | — | — | — |
| State allowed to stand for 1 month | o | o |  |  |  | x | x | x |

In an emulsion using casein Na as protein, the change rate of the average particle size of the emulsion in a range of pH 4.5 to 6.5 was suppressed to less than 1.5, and separation did not occur even after standing for 1 month. However, when the pH was set to 4.0 or less, the emulsified particles coalesced and caused oil phase separation.

Therefore, an emulsion using casein Na enhances stability of the emulsion by lowering the pH toward the isoelectric point 4.6 for casein Na (approaching the isoelectric point), and when the pH was further lowered and the isoelectric point was exceeded (going away from the isoelectric point), it was found that emulsion stability was lost and oil phase separation occurred.

TABLE 2

Alkali-treated Gelatin (Tradename: BP-250F, Source: Nippi) (Isoelectric point: 5.0)

|  | Examples | | | | | | Comp. Exs. | |
|---|---|---|---|---|---|---|---|---|
|  | 2-1 | 2-2 | 2-3 | 2-4 | 2-5 | 2-6 | 2-1 | 2-2 |
| pH | 6.5 | 6.0 | 5.5 | 5.0 | 4.5 | 4.0 | 3.5 | 3.0 |
| Particle size the day after | 21.8 | 25.4 | 11.3 | 10.7 | 20.6 | 47.1 | 66.0 | Separated |
| Particle size 2 weeks after | 10.9 | 14.6 | 11.1 | 12.6 | 20.3 | 47.6 | Separated | Separated |
| Rate of Change | 0.50 | 0.57 | 0.98 | 1.18 | 0.99 | 1.01 | — | — |
| State allowed to stand for 1 month | o | o |  |  |  |  | x | x |

An emulsion using alkali-treated gelatin as a protein did not separate after standing for one month when in a range of pH 4.0 to 6.5. At a pH of 3.5 or less, the emulsified particles coalesced and resulted in oil phase separation.

These results show that stability was increased in the emulsion using an alkali-treated gelatin about an isoelectric point of 5.0, and when the pH is 3.5 or less, it was found that the stability of the emulsion is lost and oil phase separation occurred.

TABLE 3

Whey Protein (Tradename: Sun Hope AC-2, Source: San-Ei Gen F. F. I. Inc.) (Isoelectric point: 4.6)

|  | Comp. Ex. | | Example | | | | Comp. Ex. | |
|---|---|---|---|---|---|---|---|---|
|  | 3-1 | 3-2 | 3-1 | 3-2 | 3-3 | 3-4 | 3-3 | 3-4 |
| pH | 6.5 | 6.0 | 5.5 | 5.0 | 4.5 | 4.0 | 3.5 | 3.0 |
| Particle size the day after | 5.6 | 11.5 | 16.0 | 29.4 | 31.5 | 23.9 | 34.1 | Separated |
| Particle size 2 weeks after | 15.5 | 19.1 | 20.2 | 29.2 | 32.7 | 24.9 | 45.4 | Separated |
| Rate of Change | 2.78 | 1.66 | 1.26 | 0.99 | 1.04 | 1.04 | 1.33 | — |
| State allowed to stand for 1 month | o | o | o | o | o | o | x | x |

Although an emulsion using whey protein as the protein did not separate even after standing for 1 month when in the range of pH 4.0 to 6.5, when in a range of pH 6.5 to pH 6.0, the rate of change in the particle diameter exceeded 1.5, and no improvement in stability was observed. Furthermore, when the pH was adjusted to 3.5 or less, the emulsified particles coalesced and caused oil phase separation.

These results show that emulsion stability was improved by lowering (approaching) the pH to near the isoelectric point in an emulsion using whey protein.

TABLE 4

Acid-soluble Soy Protein (Tradename: Soyasour 4000R, Source: Fuji Oil Co., LTD.) (Isoelectric point: 4.5)

|  | Comp. Ex. | Example | | | |
|---|---|---|---|---|---|
|  | 4-1 | 4-1 | 4-2 | 4-3 | 4-4 |
| pH | 6.5 | 5.0 | 4.5 | 4.0 | 3.5 |
| Particle size the day after | 76.1 | 26.1 | 24.3 | 34.6 | 41.2 |
| Particle size 2 weeks after | Separated | 24.2 | 21.9 | 33.6 | 37.7 |
| Rate of Change | — | 0.93 | 0.90 | 0.97 | 0.91 |
| State allowed to stand for 1 month | x | ? | ? | ? | ? |

TABLE 5

Soy Protein (Tradename: Fuji pro-F, Source: Fuji Oil Co., LTD.) (Isoelectric point: 4.1)

|  | Comp. Ex. | Example | | | |
|---|---|---|---|---|---|
|  | 5-1 | 5-1 | 5-2 | 5-3 | 5-4 |
| pH | 6.5 | 5.0 | 4.5 | 4.0 | 3.5 |
| Particle size the day after | 36.2 | 24.7 | 16.6 | 30.5 | 38.0 |
| Particle size 2 weeks after | 36.9 | 22.4 | 17.8 | 30.2 | 39.1 |
| Rate of Change | 1.02 | 0.91 | 1.07 | 0.99 | 1.03 |
| State allowed to stand for 1 month | x | ? | ? | ? | ? |

An emulsion using an acidic soluble soy protein or soy protein as a protein did not undergo separation after standing for 1 month in the range of pH 3.5 to 5.0, and changes in the average particle size were also suppressed. In addition, it was found that the emulsified particles coalesced at a pH of 5.5 or more or pH 3.0 and oil phase separation occurred.

Comparative Example 6: Preparation of Emulsion with Protein Solution Alone

Protein was dissolved in ion-exchanged water at room temperature to a form a concentration of 0.2%, and the pH was adjusted to 6.5 to 7.0 using an aqueous solution of NaOH. Phenoxy ethanol was added and mixed to 0.2% as a preservative.

Thereafter, ODO was added to the prepared protein solution at a mass ratio of 4:1, and homomixer treatment was performed at 9000 rpm for 3 minutes to obtain an O/W emulsion.

The median diameter of the emulsion the day after, and two weeks after, the preparation of the resulting emulsion was measured by the same method as above.

Further, the emulsion was allowed to stand at room temperature (25° C.) for 2 weeks, and the state of emulsification was visually confirmed.

The results are shown in Table 6.

TABLE 6

|  | Casein Sodium | Alkali-treated Gelatin | Acid-treated Gelatin | Whey Protein | Acid-soluble Soy Protein | Soy Protein |
|---|---|---|---|---|---|---|
| Particle size the clay after | 19.3 | 93.3 | 161.9 | 29.0 | 203.6 | 39.041 |
| Particle size 2 weeks after | Separated | Separated | Separated | Separated | Separated | 77.5 |
| State allowed to stand for 2 weeks | Separated | Separated | Separated | Separated | Separated | Separated |

Emulsions prepared with the protein solution alone without anionic polysaccharide were confirmed to not create a stable emulsion, and all emulsions resulted in oil separation after standing for 2 weeks.

Example B (Preparation of Mixed Solution of Xanthan Gum and Whey Protein)

Xanthan gum (Tradename: San Ace C, Source: San-Ei Gen F. F. I. Inc.) was added to ion-exchanged water heated to 80° C. to a concentration of 0.167%, and dissolved by stirring for 10 minutes at 80° C., and then cooled to room temperature.

Alternatively, whey protein (Tradename: San Ace C, Source: San-Ei Gen F. F. I. Inc.) was dissolved in ion exchanged water at room temperature to a concentration of 2.0% and the obtained solution was adjusted the pH to 6.5 to 7.0 with an aqueous solution of NaOH.

The resulting xanthan gum aqueous solution and protein solution were mixed at a mass ratio of 9:1, and the obtained mixed solution was stirred at 400 rpm for 10 minutes until uniform using a four-blade screw. The mixed solution was homomixer-treated at 9000 rpm for 3 minutes to obtain water-soluble or water-dispersible microparticles. At this time, an aqueous citric acid solution was added to the mixed solution during homomixer treatment to adjust the pH to 5.2

Preparation of Emulsion

ODO (oil phase) was added to the mixed solutions (water phase) of the resulting xanthan gum and protein at a mass ratio of 9:1, 8:2, 7:3, 6:4, 5:5, 4:6, and 3:7, and the obtained mixture was homomixer-treated at 9000 rpm for 3 minutes to obtain O/W type emulsion.

The obtained emulsion was allowed to stand at room temperature (25° C.) for 1 week for visual confirmation of the state of emulsification.

The median diameter (units: μm) of the emulsion after one week was measured with a laser diffraction type particle size distribution analyzer SALD-2100 (manufactured by Shimadzu Corp.).

The results are shown in Table 7.

TABLE 7

| | Examples | | | | | | |
|---|---|---|---|---|---|---|---|
| | 6-1 | 6-2 | 6-3 | 6-4 | 6-5 | 6-6 | 6-7 |
| Water Phase (part by mass) | 9 | 8 | 7 | 6 | 5 | 4 | 3 |
| Oil Phase (part by mass) | 1 | 2 | 3 | 4 | 5 | 6 | 7 |
| Particle size 1 week after (μ.m) | 15.7 | 23.2 | 22.1 | 21.5 | 17.1 | 19.3 | 15.4 |
| State allowed to stand for 1 week | unseparated | unseparated | unseparated | unseparated | unseparated | unseparated | unseparated |

In the range of water phase:oil phase=9:1 to 3:7, separation did not occur for one week, and median diameter was maintained at 30 μm or less.

Example C (Preparation of Mixed Solution of Polysaccharide other than Xanthan Gum, and Whey Protein)

A mixed solution was prepared with the same method as Example A using welan gum, pectin, CMC sodium and sodium alginate as an anionic polysaccharide and using neutral polysaccharides such as locust bean gum and guar gum as comparative examples. Each polysaccharide solution was prepared to a concentration of 0.167% (0.333% only for sodium alginate solution) and whey protein solution was prepared to a concentration of 2.0% (trade name: San Ace C; source: San-Ei Gen FFI Inc.). While homomixer treating on the mixed solution of the polysaccharide and the whey protein, and an aqueous citric acid solution was added to adjust the pH to 5.0.

(Preparation of Emulsion)

ODO (oil phase) was added to the resulting mixed solution (water phase) at a mass ratio of 4:1 and the obtained mixture was homomixer-treated at 9000 rpm for 3 minutes to obtain an O/W type emulsion.

The emulsion was allowed to stand at room temperature for 1 week for visual confirmation of the state of emulsification.

The median diameter (units: μm) of the resulting emulsion the day after preparation, and after standing for one week, was measured with a laser diffraction type particle size distribution analyzer SALD-2100 (manufactured by Shimadzu Corp.).

The results are shown in Table 8.

⊚: No separation,
○: Bottom transparency occurred,
x: Separated.

TABLE 8

|  | Example 7 | | | | | Comparative Example 7 | | |
| --- | --- | --- | --- | --- | --- | --- | --- | --- |
|  | Xanthan Gum | Welan Gum | Pectin | CMC Na | Sodium Alginate | Whey Protein only | Locust Bean Gum | Guar Gum |
| Particle size the day after | 24.3 | 31.3 | 42.4 | 37.5 | 43.3 | 29.0 | 40.0 | 24.0 |
| Particle size after 1 week | 31.0 | 37.4 | 49.1 | 41.9 | 44.9 | 49.0 | 92.8 | 47.5 |
| State allowed to stand for 1 week | ◎ | ◎ | O | O | O | X | X | X |

Example D: Preparation of Mayonnaise-Style Seasoning

A mayonnaise-style seasoning (Example 8) was prepared according to the formulation shown in Table 9 and the method shown below (all % values in the formulation mean mass%).

TABLE 9

| 1 | Salad oil | 65.0% |
| --- | --- | --- |
| 2 | Fermented Vinegar (Acid Degree 10 %) | 4.3% |
| 3 | Sugar | 2.5% |
| 4 | Sodium Chloride | 1.7% |
| 5 | L-Sodium Glutamate | 0.3% |
| 6 | Microparticle Solution* | 25.0% |
|  | Total by Ion-exchanged water | 100% |

*The microparticle solution was prepared according to Example A in the following manner with 0.5% xanthan gum (Trade name: San Ace C, Source: San-Ei Gen F.F.I. Inc.), 0.29% carrageenan (Trade name: Carrageenin CSL-2 (F), Source: San-Ei Gen F.F.I. Inc.), 0.4% whey protein (Trade name: San Hope AC-2, Source: San-Ei Gen F.F.I. Inc.).

(1) Xanthan gum and carrageenan were added to ion-exchanged water heated to 80° C. so as to be 0.56% and 0.31%, respectively, and dissolved by stirring for 10 minutes, and the sodium chloride was added thereto and then cooled to room temperature.
(2) Whey protein was added to ion-exchanged water so as to be 4.0%, and dissolved by stirring at room temperature, and 1M NaOH was added to adjust to pH 6.6.
(3) (1) and (2) were mixed at a mass ratio of 9:1.
(4) While the above mixture was treated with a homo-mixer (10000 rpm, 5 minutes), pH thereof was adjusted to 4.9 with a 50% aqueous citric acid solution to obtain a microparticle solution.
(5) The above microparticle solution was heat-treated (85° C. for 30 minutes), and then cooled to ambient temperature.
(6) 3 and 5 were dissolved in the above microparticle solution.
(7) While the resulting mixture was treated with homo-mixer (5000 rpm to 10000 rpm), 2 and 1 were added to the mixture. The resulting mixture was stirred at 10000 rpm for 5 minutes.
(8) The resulting mixture was subjected to colloid milling (slit width 500 μm, rotational speed 3000 rpm).
(9) A container was filled with a mayonnaise-like seasoning obtained by degassing.
A comparative example to the above mayonnaise-like seasoning (Example 8) was prepared as a seasoning (Comparative Example 8) according to the formulation of Table 10 (all % values in the formulation mean mass %).

TABLE 10

| 1 | Salad Oil | 65.0% |
| --- | --- | --- |
| 2 | Egg Yolk | 9.0% |
| 3 | Fermented Vinegar (Acid Degree 10 %) | 4.3% |
| 4 | Sugar | 2.5% |
| 5 | Sodium Chloride | 1.7% |
| 6 | L-Sodium Glutamate | 0.3% |
| 7 | Xanthan Gum (Sun Ace C) | 0.1% |
|  | Total by Ion-exchanged water | 100% |

(1) 7 was added to ion-exchanged water and dissolved by heatingat 80° C. for 10 minutes.
(2) 4, 5 and 6 were added thereto and stirred for another 5 minutes. The total amount thereof was adjusted after cooling.
(3) 2 was added thereto, after settling, 3 was added thereto, then 1 was slowly added thereto, and stirred for 5 minutes at 2500 rpm with a 4-blade screw.
(4) The resulting seasoning was subjected to colloid mill processing (slit width 500 μm, rotational speed 3000 rpm).
(5) A container was filled with a mayonnaise-like seasoning obtained by degassing.

<Evaluation of Mayonnaise-Like Seasoning>

The resulting mayonnaise-like seasonings (Example 8, Comparative Example 8) above were placed in a container for commercially available mayonnaise. Then, about 10 g of a sample was extruded from a star-shaped cap for the mayonnaise, and the shape retention characteristics were visually evaluated after 5 minutes.

As a result, as shown in FIG. 1, the mayonnaise-like seasoning of Example 8 had better shape retention than the mayonnaise-like seasoning of Comparative Example 8.

<Shear Rate Dependence of Viscosity>

The shear rate dependency of viscosity of the mayonnaise-like seasonings obtained above (Example 8 and Comparative Example 8) was measured using a fluid rheometer (ARES-LS1 manufactured by TA Instruments) (measurement temperature 20° C., jig: φ25 mm parallel plate, shear rate: $0.001 s^{-1}$ to $300 s^{-1}$).

Figure 2:
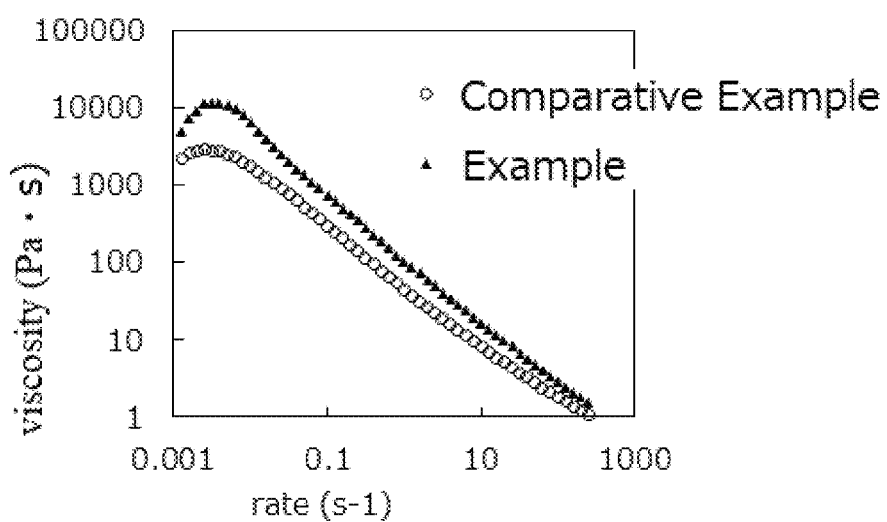
FIG. 2 is a graph of shear rate dependency measurement results using a fluid rheometer for a mayonnaise-like seasoning (Example 8 and Comparative Example 8) in Example D.

As a result, as shown in FIG. 2, the mayonnaise-like seasoning of the Example maintained a higher viscosity than the mayonnaise-like seasoning of the Comparative Example.

<Strain Dependence of Storage Modulus>

The strain dependency of the storage modulus for each of the mayonnaise-like seasonings obtained above (Example 8, Comparative Example 8) was measured using a fluid rheometer (ARES-LS1 manufactured by TA Instruments) (measurement Temperature: 20° C., jig: φ25 mm parallel plate, strain: 0.1% to 500%, frequency: 6.28 rad/s).

Figure 3:
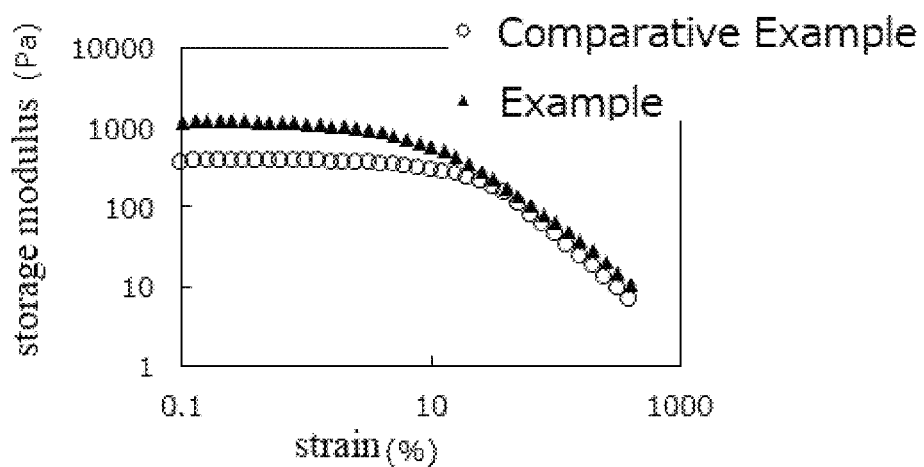
FIG. 3 is a graph of strain-dependence measurement result for a storage modulus of a mayonnaise-like seasoning (Example 8 and Comparative Example 8) in Example D.

As a result, as shown in FIG. 3, the storage modulus of the mayonnaise-like seasoning of the example was higher, and decreased from the low strain region when compared with the mayonnaise-like seasoning of the comparative example.

In light of the above experiment, it was confirmed that the microparticles obtained in the present invention exhibit a sufficient emulsifying function as an egg yolk substitute.

Example E Preparation of Dressing

A dressing (Example 9) was prepared according to the formulation shown in Table 11 and the method shown below (all % values in the formulation mean mass %).

TABLE 11

| 1 | Salad oil | 35.0% |
|---|---|---|
| 2 | Fermented Vinegar (Acid Degree 10 %) | 5.25% |
| 3 | Sugar | 5.0% |
| 4 | Sodium Chloride | 3.0% |
| 5 | L-Sodium Glutamate | 0.4% |
| 6 | Microparticle Solution* | 50.0% |
|   | Total by Ion-exchanged water | 100% |

*The microparticle solution was prepared according to Example A in the following manner with 0.5% xanthan gum (Trade name: San Ace C, Source: San-Ei Gen F.F.I. Inc.), 0.29% carrageenan (Trade name: Carrageenin CSL-2 (F), Source: San-Ei Gen F.F.I. Inc.), 0.4% whey protein (Trade name: San Hope AC-2, Source: San-Ei Gen F.F.I. Inc.).

(1) Xanthan gum and carrageenan were added to ion-exchanged water heated to 80° C. so as to be 0.56% and 0.31%, respectively, and dissolved by stirring for 10 minutes, 4 was added thereto and then cooled to room temperature.

(2) Whey protein was added to ion-exchanged water so as to be 4.0% and dissolved at room temperature by stirring for 10 minutes, and 1 M NaOH was added thereto to adjust to pH 6.6.

(3) (1) and (2) were mixed at a mass ratio of 9:1.

(4) While the above mixture was treated with a homomixer (10000 rpm, 5 minutes), pH thereof was adjusted to 4.9 with a 50% aqueous citric acid solution.

(5) The above microparticle solution of the above was heat-treated (85° C. for 30 minutes).

(6) 2, 3 and 5 were added to the microparticle solution of the above while stirring for 3 minutes in order to dissolve.

(7) The resulting mixture was cooled to ambient temperature, and then the total amount was corrected. Thereafter, while the homomixer was applied to the mixture, 1 was gradually added thereto, and stirring was performed for 5 minutes (homomixer 3000 rpm).

(8) A container was filled with a dressing obtained by degassing.

A dressing (comparative example 9) was prepared according to the formulation shown in Table 12 as a comparative example for the above dressing (all % values in the formulation mean mass %).

TABLE 12

| 1 | Salad oil | 35.0% |
|---|---|---|
| 2 | Fermented Vinegar (Acid Degree 10 %) | 5.25% |
| 3 | Sugar | 5.0% |
| 4 | Sodium Chloride | 3.0% |
| 5 | L-Sodium Glutamate | 0.4% |
| 6 | Xanthan Gum (Sun Ace C) | 0.30% |
| 7 | Egg Yolk | 2.0% |
|   | Total using Ion-exchanged water | 100% |

(1) 6 was added to water, and dissolved by stirring at 80° C. for 10 minutes.
(2) 2 to 5 were added to the resulting solution, and dissolved by stirring for 3 minutes.
(3) The resulting mixture was adjusted to 20° C. and then 7 was added thereto.
(4) After correcting the total amount thereof, 1 was gradually added while applying a homomixer. After adding the whole amount of 1, the resulting mixture was stirred for 10 minutes at 10000 rpm.
(5) The obtained dressing was degassed and filled into a container.

<Observation of Dressing>
The resulting dressings (Example 9, Comparative Example 9) were observed with an optical microscope (magnification: ×150).

Figure 4:
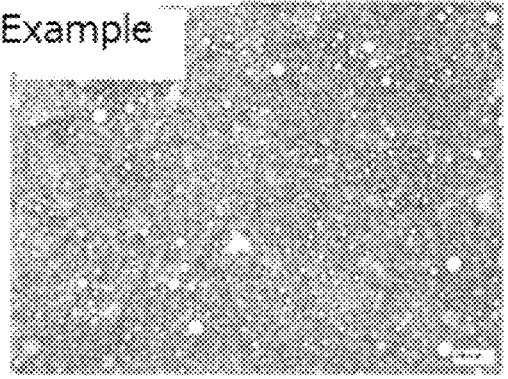
FIG. 4 is a photograph showing observation results (left: Comparative Example 9, right: Example 9) using an optical microscope (magnification: x150) of a dressing in Example E.
Figure 4:
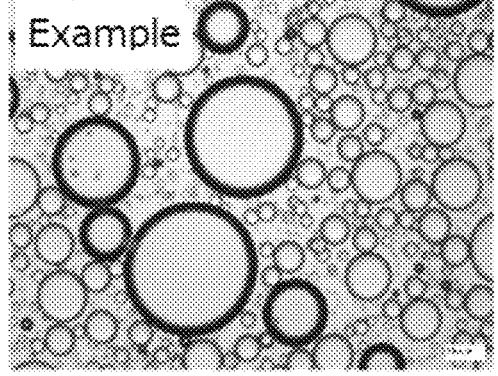

As a result, as shown in FIG. 4, the dressing of Example 9 maintained a very large oil droplet diameter when compared with Comparative Example 9, and was close to the state immediately after the separate-type dressing was mixed by repeated inversion.

<Measurement of Viscosity and Median Diameter>
The viscosity of the resulting dressing (Example 9, Comparative Example 9) at 20° C. was measured using a B-type viscometer (TVB-10M, manufactured by Toki Sangyo Co., Ltd.) at a rotational speed of 6 rpm and 60 rpm. The median diameter (units: μm) of the dressing obtained on the day of preparation, two weeks after storage at 40° C., and one month after storage at 40° C. was measured using a laser diffraction particle size distribution meter (manufactured by Shimadzu Corp., SALD-2100).

The results are shown in Table 13.

TABLE 13

| | Viscosity (mPa·s) | | Median Diameter (μm) | | |
|---|---|---|---|---|---|
| | 6 rpm | 60 rpm | On the Day | After 2 W at 40° C. | After 1 M at 40° C. |
| Ex. 9 | 4,259 | 867 | 103.0 | 103.3 | 107.4 |
| Comp. Ex. 9 | 4,188 | 873 | 10.4 | 11.9 | 10.7 |

The results shown in Table 13 show that although the dressing in Example 9 exhibited stability equivalent to the dressing in Comparative Example 9, the large particle diameter of the dressing in Example 9 resulted in a superior flavor that was similar to a separate-type dressing.

In addition, the stability and flavoring of general dressings are known to differ by type as shown below.

Emulsified-type dressing: stability ○ (not separated), flavor retention×,

Separated-type dressing: stability x (separated), flavor retention○

From this experiment, it was confirmed that the microparticles obtained in the present invention have a sufficient emulsifying function as an egg yolk substitute.

Example F: Preparation of Mixed Solution of Polysaccharide and Protein

Xanthan gum (Tradename: San Ace C, Source: San-Ei Gen F. F. I. Inc.) or soybean polysaccharide (Tradename: SM-700, Source: San-Ei Gen F. F. I. Inc.) were added to ion-exchanged water heated to 80° C. so as to the concentration as shown in Table 14 after mixing with a protein solution, was dissolved by stirring for 10 minutes at 80° C., and then cooled to room temperature.

On the other hand, whey protein (Tradename: Sun Hope AC-2, Source: San-Ei Gen F. F. I. Inc.) was dissolved in deionized water at room temperature to obtain the concentrations (unit: mass % in aqueous phase) shown in Table 14 after mixing with the polysaccharide dispersion, and the pH thereof was adjusted to 6.5 to 7.0 with an aqueous NaOH solution.

The resulting polysaccharide dispersion and the protein solution were mixed and stirred with a four-blade screw at 400 rpm for 10 minutes until uniform. The mixed solution was subjected to homomixer treatment at 9000 rpm for 3 minutes to obtain water-soluble or water-dispersible microparticles. At this time, an aqueous citric acid solution was added thereto during agitating with a homomixer, and the pH was adjusted to 5.2.

TABLE 14

| | Concentration (%) | | | Polysaccharide: |
| | Xanthan Gum | Soybean Polysaccharide | Whey Protein | Protein (mass ratio) |
|---|---|---|---|---|
| Ex. 10 | 0.5 | 0 | 0.5 | 50:50 |
| Ex. 11 | 1 | 0 | 1 | 50:50 |
| Ex. 12 | 2 | 0 | 1.3 | 61:39 |
| Ex. 13 | 0.05 | 0 | 0.1 | 33:67 |
| Ex. 14 | 0.15 | 0 | 0.2 | 43:57 |
| Ex. 15 | 0.025 | 0 | 0.05 | 33:67 |
| Ex. 16 | 0.01 | 0 | 0.02 | 33:67 |
| Ex. 17 | 0.15 | 0 | 0.4 | 27:73 |
| Ex. 18 | 0.15 | 0 | 1 | 13:87 |
| Ex. 19 | 0.5 | 0 | 0.2 | 71:29 |
| Ex. 20 | 1 | 0 | 0.2 | 83:17 |
| Ex. 21 | 1 | 0 | 0.05 | 95:5 |
| Ex. 22 | 0 | 0.5 | 0.2 | 71:29 |
| Ex. 23 | 0 | 1 | 0.2 | 83:17 |

(Preparation of Emulsion)

An ODO (oil phase) was added to resulting mixed solutions (water phase) of polysaccharide and protein to have a mass ratio of 100:5, and homomixer-treated at 9000 rpm for 3 minutes to obtain an O/W emulsions.

The resulting emulsions were allowed to stand at room temperature (25° C.) for one week, and the state of emulsifications was visually confirmed.

Furthermore, the median diameter (units: um) of the emulsions after one week was measured with a laser diffraction type particle size distribution analyzer SALD-2100 (manufactured by Shimadzu Corporation).

The results are shown in Table 15.

An emulsion prepared by the above method from a mixed solution of a 0.001% xanthan gum dispersion and a 0.02% whey protein solution, and an emulsion prepared by the above method from a mixed solution of a 0.05% xanthan gum dispersion and a 0.005% whey protein dispersion both exhibited oil floating and an unstable emulsion a short time after preparation.

The "rate of change" in Table 15 is obtained by dividing the average particle size one week after preparation by the median size on the day of preparation.

In addition, evaluation of the separation state was determined based on the following criteria.

In Table 15, "separation" means a state in which separation (oil float) of the oil phase is observed by coalescence of the emulsified particles, and redispersion does not occur even when stirred. The term "bottom transparency" means that emulsified particles float up due to the difference in specific gravity between the oil phase and the water phase, a layer consisting only of the water phase, which is the dispersion medium, is formed, and the original state is recreated easily through redispersion upon light stirring. In this case, the emulsified particles are not broken up and the emulsion remains stable. "No separation" means that separation of the oil phase does not produce bottom transparency as a result of creaming, and denotes a state in which the oil phase is uniformly dispersed in the aqueous phase, that is to say, there is a stable emulsified state.

In the table:
⊚: no separation,
○: Bottom transparency has occurred,
x: Separated.

TABLE 15

| | Median Diameter (μm) | | Rate of | State of emulsion |
| | On the Day | After 1 week | Change | after 1 month |
|---|---|---|---|---|
| Ex. 24 | 6.0 | 6.0 | 1.00 | ⊚ |
| Ex. 25 | 7.5 | 7.6 | 1.02 | ⊚ |
| Ex. 26 | 6.5 | 6.6 | 1.01 | ⊚ |
| Ex. 27 | 39.6 | 33.9 | 0.86 | ○ |
| Ex. 28 | 7.9 | 9.6 | 1.21 | ⊚ |
| Ex. 29 | 50.7 | 49.8 | 0.98 | ○ |
| Ex. 30 | 41.5 | 40.6 | 0.98 | ○ |
| Ex. 31 | 9.0 | 9.8 | 1.09 | ⊚ |
| Ex. 32 | 5.2 | 6.0 | 1.14 | ⊚ |
| Ex. 33 | 10.2 | 10.1 | 0.99 | ⊚ |
| Ex. 34 | 13.3 | 13.3 | 1.00 | ⊚ |
| Ex. 35 | 8.4 | 8.6 | 1.03 | ⊚ |
| Ex. 36 | 19.6 | 18.9 | 0.97 | ○ |
| Ex. 37 | 21.9 | 20.1 | 0.91 | ○ |

Example G Preparation of Liquid Seasoning (Pasta Sauce)

Pasta sauces (Examples 38 to 40 and Comparative Example 10) were prepared according to the method for Table 16 (all % values in the formulation mean mass %).

TABLE 16

| | Examples | | | Comp. Ex. |
| | 38 | 39 | 40 | 10 |
|---|---|---|---|---|
| Olive Oil | 25% | 25% | 25% | 25% |
| Sodium Chloride | 10% | 10% | 10% | 10% |
| Lemon Transparent Juice | 10% | 10% | 10% | 10% |
| White Wine Extract (10-fold conc.) | 2.1% | 2.1% | 2.1% | 2.1% |
| White Pepper | 1.4% | 1.4% | 1.4% | 1.4% |
| Seasoning (Sun Like Amino Base UR(N)) | 2.1% | 2.1% | 2.1% | 2.1% |
| Seasoning (Sun Like Chicken Consomme) | 2.1% | 2.1% | 2.1% | 2.1% |
| Xanthan gum (Sun Ace) | 0.1% | 0.1% | 0.1% | 0.1% |
| Whey protein (Sun Hope AC-2) | 0.01% | 0.1% | 0.2% | — |
| Flavoring (Basil SP-71887) | 0.5% | 0.5% | 0.5% | 0.5% |
| Total by ion exchanged water | 100% | 100% | 100% | 100% |

(1) Xanthan gum was added to 30 parts of ion-exchanged water and dissolved by stirring for 10 minutes.

(2) Whey protein was added to the remaining ion-exchanged water and dissolved by stirring, and the pH of the resulting solution was adjusted to 6.6 with 1M NaOH.

(3) After mixing (1) and (2), sodium chloride, lemon transparent juice, white wine extract, white pepper, seasoning and flavoring were added thereto, and the total amount of the resulting solution was made 100 with ion exchanged water and stirred for 10 minutes (pH 4 .0).

(4) After filling (3) into a container, olive oil was added thereto.

(5) After heating the container at 85° C. for 30 minutes, cooling the container to 20° C. was performed.

The container was shaken up and down 5 times, and the dispersion stability of the oil (olive oil) was evaluated. As a result, oil separation in Examples 38 to 40 was not observed even after passage of 1 hour after mixing of the oil by shaking the container. On the other hand, the oil in Comparative Example 10 started to separate immediately after shaking the container, and the oil was completely separated after 5 minutes.

Figure 5:
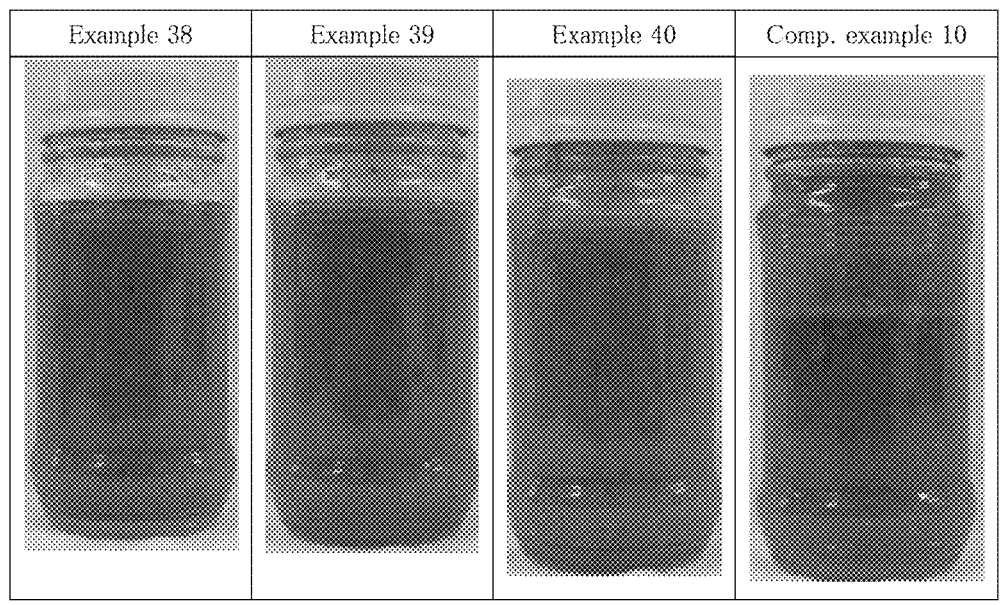
FIG. 5 is a photograph showing a state one hour after shaking a pasta sauce container in Examples 38-40 and a Comparative Example.

The state of the pasta sauce one hour after shaking the container is shown in FIG. 5.

The invention claimed is:

1. A method for producing water-soluble or water-dispersible microparticles, the method comprising;
   preparing a solution or dispersion that contains a protein and an anionic polysaccharide and that has a pH higher than the isoelectric point of the protein, and
   without addition of oil, mixing the solution or dispersion to set the pH of the solution or dispersion to a value closer to the isoelectric point, thereby forming water-soluble or water-dispersible microparticles consisting of the protein and the anionic polysaccharide,
   wherein a diameter of the formed microparticles is 50 nm to 500 µm.

2. The method for producing water-soluble or water-dispersible microparticles ticles as claimed in claim 1, wherein
   the preparation of the solution or dispersion includes the steps of
   preparing a solution of protein,
   preparing a solution or dispersion of anionic polysaccharides, and
   obtaining a mixed solution containing the protein and an anionic polysaccharide while maintaining a pH that is higher than the isoelectric point of the protein.

3. The method for producing water-soluble or water-dispersible microparticles as claimed in claim 2, wherein
   the protein solution is prepared at a pH higher than the isoelectric point of the protein.

4. The method for producing water-soluble or water-dispersible microparticles as claimed in claim 3, wherein
   the protein solution is prepared at a pH that is greater than or equal to a value that is one higher than the isoelectric point of the protein.

5. The method for producing water-soluble or water-dispersible microparticles as claimed in claim 1, wherein
   the protein solution is prepared at a concentration of 0.01 w/w % to 5 w/w %.

6. The method for producing water-soluble or water-dispersible microparticles as claimed in claim 1, wherein
   the solution or dispersion of the anionic polysaccharide is prepared at a concentration of 0.005 w/w % to 5 w/w %.

7. The method for producing water-soluble or water-dispersible microparticles as claimed in claim 1, wherein
   the protein and the anionic polysaccharide are mixed at a mass of 2:98 to 95:5.

8. The method for producing water-soluble or water-dispersible microparticles as claimed in claim 1, wherein
   in the step of mixing the solution or dispersion to set the pH of the solution or dispersion to a value closer to the isoelectric point, the solution or dispersion is mixed after setting the pH of the solution or dispersion to a value closer to the isoelectric point.

9. The method for producing water-soluble or water-dispersible microparticles as claimed in claim 1, wherein
   in the step of mixing the solution or dispersion and setting the pH of the solution or dispersion to a value closer to the isoelectric point, a homomixer is used for the mixing.

10. The method for producing water-soluble or water-dispersible microparticles as claimed in claim 1, wherein
    the protein is at least one selected from the group consisting of casein sodium, alkali-treated gelatin, acid-treated gelatin, whey protein, soy protein, acid-soluble soy protein and pea protein.

11. The method for producing water-soluble or water-dispersible microparticles as claimed in claim 1, wherein
    the anionic polysaccharide is at least one selected from the group consisting of xanthan gum, welan gum, carrageenan, deacylated gellan gum, native gellan gum, rhamsan gum, pectin, alginic acid, alginate, tragacanth gum, gati gum, gum arabic, arabinogalactan, karaya gum, succino glycans, cellulose derivatives, starch derivatives and soybean polysaccharides.

12. An emulsifying functional substitute for egg yolk, comprising: the water-soluble or water-dispersible microparticles obtained by the method of claim 1.

13. A method, comprising emulsifying a substance with the water-soluble or water-dispersible microparticles obtained by the method of claim 1.

14. A method for producing an emulsion comprising:
    mixing a combination of an oil with the water-soluble or water-dispersible microparticles obtained by the method of claim 1.

15. The method for producing an emulsion as claimed in 14, wherein
    the emulsion is a substitute for the emulsifying function of egg yolk.

16. A method for producing a food comprising adding the emulsion obtained by the method for producing an emulsion of claim 14.

17. A food comprising the emulsion obtained by the method for producing an emulsion of claim 14.

18. The method for producing water-soluble or water-dispersible microparticles as claimed in claim 1, wherein a rate of change in an average particle diameter of an emulsion consisting of an oil and the water-soluble or water dispersible microparticles is less than 1.5 where the rate of change is determined by dividing the average particle diameter measured two weeks after preparation of the emulsion by the median diameter measured on the day of preparation.

* * * * *